United States Patent
Breton

(10) Patent No.: US 6,994,864 B2
(45) Date of Patent: *Feb. 7, 2006

(54) COMPOSITION CONTAINING 7-HYDROXY DHEA AND/OR 7-KETO DHEA AND AT LEAST A CAROTENOID

(75) Inventor: Lionel Breton, Versailles (FR)

(73) Assignee: L'Oreal, Paris (FR)

(*) Notice: Subject to any disclaimer, the term of this patent is extended or adjusted under 35 U.S.C. 154(b) by 226 days.

This patent is subject to a terminal disclaimer.

(21) Appl. No.: 10/433,490

(22) PCT Filed: Nov. 20, 2001

(86) PCT No.: PCT/FR01/03643

§ 371 (c)(1),
(2), (4) Date: Nov. 5, 2003

(87) PCT Pub. No.: WO02/47649

PCT Pub. Date: Jun. 20, 2002

(65) Prior Publication Data

US 2004/0077722 A1 Apr. 22, 2004

(30) Foreign Application Priority Data

Dec. 15, 2000 (FR) .............................. 00 16436

(51) Int. Cl.
*A61K 7/00* (2006.01)
*A61K 7/42* (2006.01)
*A61K 7/44* (2006.01)
*A61K 35/78* (2006.01)

(52) U.S. Cl. .................. 424/401; 424/59; 424/60; 424/400; 424/725

(58) Field of Classification Search .............. 424/59, 424/60, 400, 401, 725
See application file for complete search history.

(56) References Cited

U.S. PATENT DOCUMENTS

| 6,048,846 A | | 4/2000 | Cochran |
| 6,093,706 A | | 7/2000 | Zeligs |
| 6,121,243 A | * | 9/2000 | Lanzendorfer et al. ....... 514/28 |
| 2004/0072764 A1 | | 4/2004 | Breton |

FOREIGN PATENT DOCUMENTS

| DE | 44 32 947 A1 | 3/1996 |
| EP | 0 908 183 A1 | 4/1999 |
| FR | 2 765 803 A1 | 1/1999 |
| FR | 2771 105 | 5/1999 |
| FR | 2 777 182 A1 | 10/1999 |
| WO | WO 92/03925 | 3/1992 |
| WO | WO 97/03676 | 2/1997 |
| WO | WO 98/03170 | 1/1998 |
| WO | WO 98/40074 | 9/1998 |
| WO | WO 98/56373 | 12/1998 |
| WO | WO 99/07381 | 2/1999 |
| WO | WO 00/01351 | 1/2000 |
| WO | WO 00/28996 | 5/2000 |

* cited by examiner

*Primary Examiner*—Shelley A. Dodson
(74) *Attorney, Agent, or Firm*—Oblon, Spivak, McClelland, Maier & Neustadt, P.C.

(57) ABSTRACT

The invention concerns a composition containing, in a physiologically acceptable medium: (a) at least a DHEA derivative selected among 7-hydroxy DHEA and 7-keto DHEA, and (b) at least a carotenoid. The invention also concerns cosmetic and dermatological uses of said composition, in particular for preventing or treating actinic skin ageing symptoms.

22 Claims, No Drawings

COMPOSITION CONTAINING 7-HYDROXY DHEA AND/OR 7-KETO DHEA AND AT LEAST A CAROTENOID

The present invention relates to a composition containing 7-hydroxy-DHEA and/or 7-keto-DHEA and at least one carotenoid, and to the use of said composition, in particular for preventing or treating the signs of actinic skin aging.

DHEA, or dehydroepiandrosterone, is a natural steroid which is mainly produced by the corticoadrenal glands. Exogenous DHEA, administered topically or orally, is known for its capacity to promote keratinization of the epidermis (JP-07 196 467) and to treat dry skins by increasing the endogenous production and the secretion of sebum and by thus reinforcing the barrier effect of the skin (U.S. Pat. No. 4,496,556). There has also been described in Patent U.S. Pat. No. 5,843,932 the use of DHEA for treating atrophy of the dermis by inhibiting the loss of collagen and of connective tissue. Finally, the applicant has demonstrated the capacity of DHEA to control the weathered appearance of the skin (FR 00/00349), and to modulate the pigmentation of the skin and of the hair (FR 99/12773) and to control atrophy of the epidermis (FR 00/06154). These properties of DHEA make it a candidate of choice as anti-aging active agent.

Among the metabolites of DHEA, particular attention has been made in the last few years to 7α-hydroxy-DHEA. It has indeed been demonstrated that this metabolite, which does not possess the hormonal activity of DHEA, made it possible to increase the proliferation of the fibroblasts and the viability of the human keratinocytes and had anti-free radical effects (WO 98/40074). It has also been demonstrated, on rats (WO 00/28996), that 7α-hydroxy-DHEA increased the thickness of the dermis and the elastin and collagen content of the skin. It has thus been suggested to use this metabolite of DHEA for preventing and/or treating the harmful effects of UV radiation on the skin, for controlling wrinkles and for increasing skin firmness and tone.

7α-Hydroxy-DHEA is, with 5-androstene-3β,17β-diol, a major metabolite of DHEA, which is obtained by the action of 7α-hydroxylase on DHEA. Among the minor metabolites of DHEA, there may be mentioned 7β-hydroxy-DHEA, which is obtained by the action of 7β-hydroxylase on DHEA and 7-keto-DHEA, which is itself a metabolite of 7β-hydroxy-DHEA.

In the remainder of this description, the expression "7-hydroxy-DHEA" will be used to designate without distinction 7α-hydroxy-DHEA and 7β-hydroxy-DHEA.

It is now evident to the applicant that the combination of 7-hydroxy-DHEA and/or 7-keto-DHEA with a carotenoid could make it possible to more effectively prevent or treat the signs of skin aging, in particular of actinic aging or photoaging.

The subject of the present invention is therefore a composition containing, in a physiologically acceptable medium: (a) at least one DHEA derivative chosen from 7-hydroxy-DHEA and 7-keto-DHEA, and (b) at least one carotenoid.

7-Hydroxy-DHEA is preferably 7α-OH-DHEA. A method for preparing this compound is described in particular in Patent Applications FR-2 771 105 and WO 94/08588. However, 7β-OH-DHEA is also suitable for use in the present invention.

The concentration of DHEA derivative in the composition according to the invention is advantageously between 0.0000001% and 10% by weight, preferably between 0.00001% and 5% by weight, relative to the total weight of the composition.

The composition according to the present invention contains, in combination with the DHEA derivative, at least one carotenoid.

The expression carotenoid is understood to mean according to the invention both a carotenoid with provitamin A activity and a carotenoid without provitamin A activity. Among the carotenoids with provitamin A activity, there may be mentioned, by way of example, β-carotene or α-carotene. Among the carotenoids without provitamin A activity, there may be mentioned, by way of example, zeaxanthin, lutein or lycopene.

The carotenoid used according to the invention may be of natural or synthetic origin. The expression natural origin is understood to mean the carotenoid, in the pure state or in solution regardless of its concentration in said solution, obtained from a natural component. The expression synthetic origin is understood to mean the carotenoid, in the pure state or in solution regardless of its concentration in said solution, obtained by chemical synthesis.

When the carotenoid is of natural origin, it may be obtained from a plant material derived from a whole plant cultured in vivo or derived from in vitro culture. The expression in vivo culture is understood to mean any culture of the conventional type, that is to say in the soil in the open air or in a greenhouse, or alternatively with no soil. The expression in vitro culture is understood to mean all the techniques known to persons skilled in the art which artificially allow the production of a plant or of a portion of a plant. The selection pressure imposed by the physicochemical conditions during the growth of plant cells in vitro makes it possible to obtain a standardized plant material which is available throughout the year unlike plants cultured in vivo.

Preferably according to the invention, a plant derived from in vivo culture is used.

Any method of extraction known to persons skilled in the art may be used to prepare the carotenoid used according to the invention. The carotenoid may be in an alcoholic, in particular ethanolic, solution. The carotenoid may also be in a lipid (oil) or lipid-alcohol solution.

The preferred carotenoids according to the invention are β-carotene and lycopene. Most preferably, lycopene is used.

Lycopene is a natural pigment which is found in ripe fruits, particularly in tomato. Its structure is close to that of β-carotene. It may be in cis or trans form.

By way of example, according to the invention, there is used a lycopene-rich tomato extract prepared by the company Métaphar and marketed under the name LycOMato® consisting of an oleoresin extract (fatty phase) containing 6% pure lycopene.

It is also possible to use, according to the invention, any preparation containing lycopene with the objective of improving the bioavailability of the latter and any novel raw material containing lycopene obtained from a novel method of manufacture.

The quantity of carotenoid which can be used according to the invention of course depends on the desired effect and may therefore vary to a great extent.

To give an order of magnitude, in the composition according to the invention, the carotenoid in the pure state is in a quantity representing from $10^{-12}$% to 20% of the total weight of the composition and preferably in a quantity representing from $10^{-8}$% to 10% of the total weight of the composition.

Of course, persons skilled in the art, if they use the carotenoid in the form of a solution, a plant extract for example, know how to adjust the quantity of solution which they use in their composition so that the final quantity of carotenoid in the composition is consistent with the above-defined quantities which can be used.

Lycopene is in particular known as an anti-free radical agent (JP-A-8-283136).

However, as indicated above, 7α-OH-DHEA, applied by the topical route, has itself an activity on the signs of skin aging, due in particular to its anti-free radical effects.

It will therefore be appreciated that the combination of a DHEA derivative according to the invention with a carotenoid makes it possible to reinforce the anti-aging effects of the composition containing them, in particular when this involves preventing or treating the signs of actinic skin aging.

The composition according to the invention is preferably suitable for topical application to the skin. It may be provided in all the galenic forms normally used for this type of application, in particular in the form of an aqueous or oily solution, an oil-in-water or water-in-oil or multiple emulsion, a silicone emulsion, a microemulsion or nanoemulsion, an aqueous or oily gel or a liquid, pasty or solid anhydrous product.

This composition may be fluid to a greater or lesser degree and may have the appearance of a white or colored cream, an ointment, a milk, a lotion, a serum, a paste, a mousse or a gel. It may be optionally applied to the skin in aerosol form. It may also be provided in solid form, for example in the form of a stick. It may be used as a care product and/or as a make-up product for the skin.

In a known manner, the composition of the invention may also contain the customary adjuvants in the cosmetic and dermatological fields, such as hydrophilic or lipophilic gelling agents, hydrophilic or lipophilic active agents, preservatives, antioxidants, solvents, perfumes, fillers, screening agents, pigments, odor absorbers and coloring matter. The quantities of these various adjuvants are those conventionally used in the fields considered, and are for example from 0.01 to 20% of the total weight of the composition. These adjuvants, depending on their nature, can be introduced into the fatty phase or into the aqueous phase. These adjuvants, and their concentrations, should be such that they do not adversely affect the advantageous properties of the DHEA derivatives, or of the carotenoids according to the invention.

When the composition according to the invention is an emulsion, the proportion of the fatty phase may range from 5 to 80% by weight, and preferably from 5 to 50% by weight relative to the total weight of the composition. The fatty substances, the emulsifiers and the coemulsifiers used in the composition in the form of an emulsion are chosen from those conventionally used in the field considered. The emulsifier and the coemulsifier are preferably present in the composition in a proportion ranging from 0.3 to 30% by weight, and preferably from 0.5 to 20% by weight relative to the total weight of the composition.

As fatty substances which can be used in the invention, it is possible to use oils and in particular mineral oils (liquid paraffin), oils of plant origin (avocado oil, soybean oil), oils of animal origin (lanolin), synthetic oils (perhydrosqualene), silicone oils (cyclomethicone) and fluorinated oils (perfluoro-polyethers). It is also possible to use, as fatty substances, fatty alcohols such as cetyl alcohol, fatty acids, waxes and gums, and in particular silicone gums.

As emulsifiers and coemulsifiers which can be used in the invention, there may be mentioned, for example, esters of fatty acids and of polyethylene glycol such as PEG-100 stearate, PEG-50 stearate and PEG-40 stearate; esters of fatty acids and of polyols such as glyceryl stearate, sorbitan tristearate, oxyethylenated sorbitan stearates which are available under the trade names Tween® 20 or Tween® 60, for example; and mixtures thereof.

As hydrophilic gelling agents, there may be mentioned in particular carboxyvinyl polymers (carbomer), acrylic copolymers such as acrylate/alkyl acrylate copolymers, polyacrylamides, polysaccharides, natural gums and clays, and, as lipophilic gelling agents, there may be mentioned modified clays such as bentones, metal salts of fatty acids and hydrophobic silica.

According to one variant of the invention, the composition may be suitable for administration by the oral route. In this case, it may be provided in the form of syrups, suspensions, solutions, emulsions, granules, capsules or tablets, for example.

The daily doses of DHEA derivative which are administered by the oral route may be between 1 and 100 mg/day, preferably between 25 and 75 mg/day. Preferably, the DHEA derivative is present in the composition according to the invention in a quantity allowing its administration at a dose between 50 and 100 mg/day, said dosage being obtained in one or more doses, with a unit dose of 50 mg.

The daily doses of carotenoids administered by the oral route should be defined on a case by case basis, according to the carotenoid involved. More particularly, in the case of beta-carotene or lycopene, the daily doses administered may be between 1 and 500 mg/day, preferably at doses between 1 and 50 mg/day.

In all cases, the composition according to the invention and/or the preparation obtained therefrom comprises an effective quantity of DHEA derivative and an effective quantity of carotenoid, sufficient to obtain the desired effect, in a physiologically acceptable medium.

The composition according to the invention finds application in particular in the prevention and treatment of the signs of skin aging, in particular of actinic aging.

The present invention therefore also relates to the cosmetic use of the abovementioned composition for the prevention or treatment of the signs of skin aging, in particular of actinic aging.

It relates in particular to the cosmetic use of the composition described above for preventing or controlling the formation of wrinkles and/or for improving skin tone and/or for increasing skin firmness.

The present invention also relates to the cosmetic use of the composition described above for preventing or controlling the harmful effects of UV radiation on the skin.

It finally relates to the use of the composition described above for manufacturing a preparation intended for preventing or controlling the harmful effects of UV radiation on the skin.

The invention will now be illustrated by the following nonlimiting examples. In these examples, the quantities are indicated as a percentage by weight.

EXAMPLE 1

Composition for Oral Administration

Soft gelatin capsules having the following composition are prepared in a manner which is conventional for persons skilled in the art:

| | |
|---|---|
| Hydrogenated soybean oil | 40 mg |
| Wheat oil | 95 mg |
| Soybean lecithin | 20 mg |
| Natural tocopherols | 5 mg |
| Ascorbic acid | 30 mg |
| Beta-carotene | 10 mg |
| 7α-OH-DHEA | 50 mg |

EXAMPLE 2

Composition for Oral Administration

Soft gelatin capsules having the following composition are prepared in a manner which is conventional for persons skilled in the art:

| | |
|---|---|
| Hydrogenated soybean oil | 40 mg |
| Wheat oil | 95 mg |
| Soybean lecithin | 20 mg |
| Natural tocopherols | 5 mg |
| Ascorbic acid | 30 mg |
| Lycopene | 6 mg |
| 7α-OH-DHEA | 50 mg |

EXAMPLE 3

Composition for Topical Application

A care cream (oil-in-water emulsion) having the following composition is prepared in a manner which is conventional for persons skilled in the art:

| | |
|---|---|
| Lycopene at 6% | $10^{-4}$% |
| 7α-OH-DHEA | 0.1% |
| Glyceryl stearate | 2% |
| Polysorbate 60 (Tween 60 ® sold by the company ICI) | 1% |
| Stearic acid | 1.4% |
| Triethanolamine | 0.7% |
| Carbomer | 0.4% |
| Liquid fraction of shea butter | 12% |
| Perhydrosqualene | 12% |
| Perfume | 0.5% |
| Preservative | qs |
| Water | qs 100% |

What is claimed is:

1. A composition comprising:
   a physiologically acceptable medium;
   at least one DHEA derivative; selected from the group consisting of 7-hydroxy-DHEA and 7-keto DHEA; and
   at least one carotenoid.

2. The composition as claimed in claim 1, comprising 7α-OH-DHEA.

3. The composition as claimed in claim 1, comprising 7β-OH-DHEA.

4. The composition as claimed in claim 1, wherein said carotenoid is at least one of a natural carotenoids or a synthetic cartenoid.

5. The composition as claimed in claim 1, wherein said carotenoid is at least one of a carotenoids with provitamin A activity or a carotenoids without provitamin A activity.

6. The composition as claimed in claim 5, comprising a carotenoid with provitamin A activity selected from the group consisting of β-carotene and α-carotene.

7. The composition as claimed in claim 6, comprising β—carotene.

8. The composition as claimed in claim 6, comprising α—carotene.

9. The composition as claimed in claim 5, comprising a carotenoid without provitamin A activity selected from the group consisting of zeaxanthin, lutein and lycopene.

10. The composition as claimed in claim 9, comprising lycopene.

11. The composition as claimed in claim 9, comprising lutein.

12. The composition as claimed in claim 9, comprising zeaxanthin.

13. The composition as claimed in claim 1, wherein the composition is for topical application to the skin.

14. The composition as claimed in claim 13, wherein the DHEA derivative is present in an amount of from 0.0000001 to 10% by weight, relative to the total weight of the composition.

15. The composition as claimed in claim 14, wherein the DHEA derivative is present in an amount of from 0.00001 to 5% by weight, relative to the total weight of the composition.

16. The composition as claimed in claim 13, wherein the cartenoid is present in an amount of from $10^{-8}$% to 10% by weight, relative to the total weight of the composition.

17. The composition as claimed in claim 1, wherein the composition is for administration by the oral route.

18. A process comprising: administering the composition of claim 1 orally.

19. A process comprising: applying the composition as claimed in claim 1 to the skin of a human in an amount effective for treating the aging of skin.

20. A process comprising: applying the composition as claimed in claim 1 to the skin of a human in an amount effective for improving skin tone or increasing skin firmness.

21. A process comprising: applying the composition as claimed in claim 1 to the skin of a human in an amount effective for reducing the harmful effects of UV radiation.

22. A process comprising: applying the composition as claimed in claim 1 to the skin of a human in an amount that is effective for alleviating the harmful effects of UV radiation on the skin.

* * * * *

UNITED STATES PATENT AND TRADEMARK OFFICE
CERTIFICATE OF CORRECTION

PATENT NO. : 6,994,864 B2
APPLICATION NO. : 10/433490
DATED : February 7, 2006
INVENTOR(S) : Lionel Breton It is certified that error appears in the above-identified patent and that said Letters Patent is hereby corrected as shown below:

Column 6, line 4 claim 4, "carotenoids" should be --carotenoid--;

line 7 claim 5, "carotenoids" should be --carotenoid--; and line 8 claim 6, "carotenoids" should be --carotenoid--.

Signed and Sealed this

Twelfth Day of February, 2008

JON W. DUDAS
*Director of the United States Patent and Trademark Office*